United States Patent [19]

Shaw

[11] Patent Number: 6,130,245

[45] Date of Patent: Oct. 10, 2000

[54] DINUCLEAR PLATINUM COMPLEXES AS CISPLATIN ANALOGS FOR CANCER TREATMENT

[75] Inventor: Jiajiu Shaw, Ann Arbor, Mich.

[73] Assignee: Unitech Pharmaceuticals, Inc., Ann Arbor, Mich.

[21] Appl. No.: 09/178,055

[22] Filed: Oct. 26, 1998

[51] Int. Cl.$^7$ ................................................. A61K 31/28
[52] U.S. Cl. ................................... 514/492; 556/137
[58] Field of Search ............................. 556/137; 514/492

[56] References Cited

U.S. PATENT DOCUMENTS

| | | | |
|---|---|---|---|
| 4,797,393 | 1/1989 | Farrell | 514/188 |
| 5,107,007 | 4/1992 | Farrell | 556/137 |

OTHER PUBLICATIONS

CA:117:62087 abs of Platinum Other Met Coord Comp Cancer Chemother, (Proc Int Symp) 6th 1991, pp. 93–100 by Giandomenico.

CA:112:69485 abs of Byull. Eksp Biol Med by Plotnikov 108(9) pp. 313–315, 1989.

CA:108:179643 abs of J Antimicrob Chemother by Wondrak 21 (2), pp. 151–161, 1988.

CA:100:167839 abs of J Am Chem Soc by Vollano 106(9) pp. 2732–2733, 1984.

CA:93:179372 abs of Cancer Res by Crook 40 (9) pp. 3318–3324, 1980.

*Primary Examiner*—Gary Geist
*Assistant Examiner*—Jean F. Vollano
*Attorney, Agent, or Firm*—Brinks Hofer Gilson & Lione

[57] ABSTRACT

This invention comprises the synthesis and the use of a new class of cisplatin analogs. These analogs are complexes formed between tetrachloroplatinum (II) and triethylenetetraamine or its derivatives. The stoichiometric ratio between cisplatin and triethylenetetraamine or its derivatives is between 0.4:1 to 0.5:0.8. The complexes are to be used in cancer treatment; they may also be used to treat AIDS patients.

4 Claims, No Drawings

DINUCLEAR PLATINUM COMPLEXES AS CISPLATIN ANALOGS FOR CANCER TREATMENT

BACKGROUND OF THE INVENTION

This invention relates to the syntheses of certain new dinuclear platinum complexes as cisplatin analogs and the use of these cisplatin analogs to treat cancer.

Cisplatin (cis-diamminedichloroplatinum, cis-Pt(NH$_3$)$_2$Cl$_2$, molecular weight 300.05) has been used as a chemotherapeutic agent for many years since the discovery of its anti-tumor activity by B. Rosenberg et. al. (*Nature*, 1965, 205, 698; *Nature*, 1972, 222, 385).

Chemical & Engineering News (Oct. 23, 1995) reported that "Cisplatin was first synthesized in the 1800s, but its anticancer activity was not discovered until the 1960s. In 1979, it was approved by the Food and Drug Administration for clinical treatment of testicular and ovarian tumors and cancers of the head and neck. Cisplatin and an analog, carboplatin, are now among the most widely used anticancer drugs."

The Physician's Desk Reference reports that cisplatin (the commercial name is Platinol®) can be used to treat testicular cancer, ovarian cancer, and bladder cancer. Rosenberg et al., U.S. Pat. No. 4,177,263, describes methods of treating cancer using cisplatin and cisplatin analogs. The compound was shown to be effective for treating leukemia and tumors induced in mice.

After so many years, cisplatin is still being widely used because of its efficacy. However, its critical drawback, the toxicity, is still a major concern. Many attempts have been made to either reduce its toxicity or increase its efficacy.

Predominantly, cisplatin binds onto deoxyguanosine of DNA. It also binds onto other deoxynucleosides or nucleosides. Because of the non-selectivity of cisplatin between cancer cells and normal cells, cisplatin has a lot of side effects. Besides, cisplatin is effective only to certain kinds of cancers. Therefore, reducing the toxicity of cisplatin and expanding its use in more cancers have been very important issues for all scientists involved in its research.

Many people have attempted to change the ligand on platinum to make new cisplatin analogs in order to reduce the toxicity or improve the efficacy. Examples are made by K. C. Tsou, et al.(*J. Clin. Hemat. Oncol.* 1977, 7, 322,), R. J. Speeder et al. (*J Clin. Hemat. Oncol.* 1977,. 7, 210), A. Mathew et. al. (*Chem. Comm.* 1979, 222), D. Rose, et al. (*Cancer Treatment Reviews*, 1985, 12, 1), and D. Alberts et al. (*Cancer Treatment Reviews*, 1985, 12, 83).

Recently, a new type of cisplatin analogs, dinuclear platinum (II) complexes, was reported by Farrell etc. (Biochemistry, 1995, 34, 15480). Farrell prepared complexes in which cisplatin was bound to the ligand by only a single Pt—N bond. All of the complexes made by Farrell had an overall charge of +2 for the cation. The examples of Farrell's complexes are [{trans-PtCl(NH$_3$)$_2$}H$_2$N(CH$_2$)$_4$NH$_2${trans-PtCl(NH$_3$)$_2$}]$^{2+}$, [{cis-PtCl(NH$_3$)$_2$}H$_2$N(CH$_2$)$_4$NH$_2${cis-PtCl(NH$_3$)$_2$}]$^{2+}$, and [{trans-PtCl(py)$_2$}H$_2$N(CH$_2$)$_4$NH$_2${trans-PtCl(py)$_2$}]$^{2+}$ where py is pyridine. The biological data for these complexes indicated that they may have higher efficacy or better specificity than cisplatin.

BRIEF SUMMARY OF THE INVENTION

This invention comprises the syntheses of a group of new cisplatin analogs, dinuclear platinum complexes, and the use of these cisplatin analogs to treat cancer.

The complexes of the present invention have the formula (I):

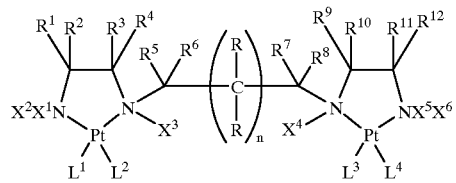

wherein n is 0, 1, 2, 3, 4, 5, or 6;
each of L$^1$, L$^2$, L$^3$, and L$^4$, independently, is Cl or Br;
each of R,R',R$^1$,R$^2$,R$^3$,R$^4$, R$^5$, R$^6$, R$^7$, R$^8$, R$^9$, R$^{10}$, R$^{11}$, and R$^{12}$, independently, is hydrogen, lower alkyl, lower alkoxy, alkyl carboxylate or alkyl carboxylic acid salt; or each of CR$^1$R$^2$(that is, R$^1$ and R$^2$ together with the carbon which they substitute), CR$^3$R$^4$, CR$^5$R$^6$, CR$^7$R$^8$, CR$^9$R$^{10}$, CR$^{11}$R$^{12}$, and CRR' independently, is C=O, and
each of X$^1$, X$^2$, X$^3$, X$^4$, X$^5$, and X$^6$, independently, is hydrogen, lower alkyl, alkyl carboxylate or alkyl carboxylic acid salt.

The dinuclear platinum complex of the present invention may have 1 to 4 Pt—Cl bonds, which are labile and responsible for binding to DNA. The overall charge for the complex may be 0, +1, and +2.

As used herein, "lower alkyl" means a linear, branched or cyclic hydrocarbon group containing from about 1 to 6 carbons, preferably from 1 to 3 carbons. Preferred lower alkyl groups include methyl, ethyl, and propyl.

"Lower alkoxy" means a linear or branched chain alkoxy group from about 1 to 6 carbons, preferably from 1 to 3 carbons. Preferred lower alkoxy groups include methoxy, ethoxy, and propoxy.

"Alkyl carboxylate" means a linear or branched hydrocarbon group containing from about 1 to 6 carbons, preferably from 1 to 3 carbons, and a carboxylate group (—COOH).

Salts of alkyl carboxylates include inorganic or organic salts such as [—CH$_2$COO]$^-$[Na]$^+$, [—(CH$_2$)$_2$COO]$^-$[N(CH$_3$)$_4$]$^+$, etc.

DETAILED DESCRIPTION OF THE INVENTION

This invention comprises the syntheses of a group of new cisplatin analogs, dinuclear platinum complexes, and the use of these cisplatin analogs to treat cancer.

The complexes of the present invention have the formula (I):

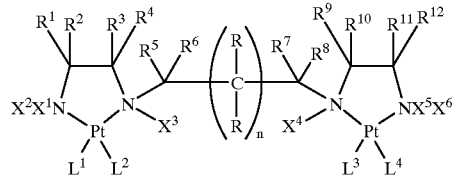

wherein n is 0, 1, 2, 3, 4, 5, or 6;
each of L$^1$, L$^2$, L$^3$, and L$^4$, independently, is Cl or Br;
each of R,R',R$^1$,R$^2$,R$^3$,R$^4$,R$^5$,R$^6$,R$^7$,R$^8$, R$^9$, R$^{10}$, R$^{11}$, and R$^{12}$, independently, is hydrogen, lower alkyl, lower alkoxy, alkyl carboxylate or alkyl carboxylic acid salt;

or each of $CR^1R^2$ (that is, $R^1$ and $R^2$ together with the carbon which they substitute), $CR^3R^4$, $CR^5R^6$, $CR^7R^8$, $CR^9R^{10}$, $CR^{11}R^{12}$, and CRR' independently, is C=O, and each of $X^1$, $X^2$, $X^3$, $X^4$, $X^5$, and $X^6$, independently, is hydrogen, lower alkyl, alkyl carboxylate or alkyl carboxylic acid salt.

The dinuclear platinum complex of the present invention may have 1 to 4 Pt—Cl bonds, which are labile and responsible for binding to DNA. The overall charge for the complex may be 0, +1, and +2.

The dinuclear complex comprises $[PtCl_4]^{+2}$ and triethylenetetraamine or its derivatives, at a stoichiometric ratio of about 1.8:1 to about 2:0.8, preferably 1.9:1 to 2 to 0.9, and most preferably at the ratio of about 2:1.

The chelating agents may include triethylenetetraamine and its derivatives. Suitable derivatives include N,N'-bis(2-dimethylaminoethyl)oxamide, N,N'-bis(2-aminoethyl)oxamide, and N,N'-bis(2-aminoethyl)ethylenediamine.

The labile Pt—Cl bonds on the new complex chelate with DNA in the same fashion that cisplatin does. Therefore, the complex may be used to treat cancer. The complex can be more powerful than cisplatin because it has two levels of chelating effects on DNA. Besides the cisplatin effects, an additional level of chelating effect exists because of the carbon chain that connects the two Pt centers. In Farrell's paper, only the latter effect was in effect because none of the Pt has a pair of cis-[Pt—Cl] bonds.

This class of cisplatin analogs maintains the original active sites of cisplatin (i.e., two Pt—Cl bonds in cis position). In addition, there is a bridge (the carbon chain) connecting the two Pt centers creating another level of chelating effect.

Specific examples of making these complexes are shown in the examples below.

Because there are two Pt in each complex, several scenarios may be explained as follow (Cl may be replaced by Br in all three scenarios): (1) one Pt—Cl bond on each Pt—In this case, each of the two Pt—Cl bonds (one on each Pt) serves as an active site of a bidentate chelating agent. (2) two Pt—Cl bonds on each Pt—In this case, each Pt has two Pt—Cl bonds in cis position, which functions as cisplatin. In addition, because the two pairs of cis-[Pt—Cl] bonds are connected by the carbon chain, each cis-[Pt—Cl] pair can act as an active site of a larger bidentate ligand and attack DNA in the way similar to that in scenario 1. (3) two Pt—Cl bonds on one Pt and one Pt—Cl bond on another Pt—In this case, one pair of cis-[Pt—Cl] bonds may act just like cisplatin does. The other Pt—Cl bond would act in coordination with the pair of cis-[Pt—Cl] bonds to form two active sites of a larger bidentate ligand.

Methods of Treatment

The complex of the present invention may be used to treat cancers including testicular cancer, ovarian cancer, bladder cancer, breast cancer, and skin cancer.

The complex may be administered to a cancer patient orally, or by subcutaneous or intravenous injection, or by means of an implanted reservoir, or by means of applying on the cancerous skin.

The injectable dosages are normally in the form of an aqueous solution. If necessary, pharmaceutically-acceptable suspension or emulsion may be employed. Typically, such a composition contains the complex at a concentration of 0.005%–0.25% (0.05 mg/mL–2.5 mg/mL), more commonly 0.01%–0.1% (0.1 mg/mL–1 mg/mL). The dosage administered by injection comprises the complex in the range of 5–1,000 mg in the first day of every 1–4 weeks depending upon the patient. Typically, one might administer a dosage of 50–400 mg in the first day of every 1–4 weeks to a patient having a body weight of 40–100 kg, although in appropriate cases such dosages may prove useful for patients having a body weight outside this range.

The complex may also be administered orally, for example, as a solution, a suspension, an emulsion, or as tablets or capsules. Solution and suspension for oral administration are typically of about the same concentration as those used for injection. However, when administering the complex orally, it may be desirable to use a higher dosage rate than when administering it by injection. For example, a dosages containing 10–1,500 mg of the complex in the first day of every 1–4 weeks may be used. Typically, one might administer a dosage containing 50–600 mg of the complex in the first day of every 1–4 weeks. In preparing such tablets or capsules, standard tablet or capsule making techniques may be employed. If desired, suitable pharmaceutically acceptable excipients such as starch, mannitol, cellulose, talc, surfactant, or lactose may be used in preparing the tablets or capsules. Capsules may also be prepared using soft gelatin as the encapsulating agent. If desired, such capsules may be in the form of sustained release capsules wherein the main capsule contains microcapsules which release the active ingredient over a period of several hours.

It may also be used in combination or in tandem with other known anticancer drugs, including but not limited to Texol®(paclitaxel) and doxorubicin.

The complex of the present invention may also be used in the treatment of AIDS (Acquired Immune Deficiency Syndrome). Because of the ability of these complexes to hamper the DNA or RNA replication process, it is likely that these complexes are effective against the HIV (Human Immunodeficiency Virus) and may be used for the treatment of AIDS.

It may also be used in combination or in tandem with other known AIDS drugs, including but not limited to AZT (3'-azidothymidine), to interfere with the HIV enzyme reverse transcriptase and achieve better results.

This complex may be administered to an AIDS patient in the same way as in the treatment of a cancer patient. A dosage containing 10–600 mg of the complex in the first day of every 1–4 weeks may be administered.

When used in conjunction with a well known drug for AIDS, such as AZT, the dosage may be suitably reduced. A dosage containing 5–1,500 mg of the complex in the first day of every 1–4 weeks may be administered; the dosage and the method of administration of said drug for AIDS is the same as it is normally used.

In conclusion, a new class of dinuclear platinum complexes is disclosed in this invention. The syntheses of this class of dinuclear platinum complexes are presented in this invention. As cisplatin analogs, they may be used to treat cancer. They may also be used for the treatment of cancer and AIDS.

Although the description above contains many specificities, these should not be construed as limiting the scope of the invention but as merely providing the illustrations of some of the presently preferred embodiments of this invention. For example, the compounds can be made in pure water instead of the mixture of methanol and water.

EXAMPLES

Example 1

2:1 Complex of tetrachloroplatinum (II) and triethylenetetraamine

A 0.01 molar aqueous solution of tetraethylenetetraamine (e.g., 0.073 g in 50 mL) was slowly added into a 0.02 M aqueous solution of potassium tetrachloroplatinum (II), light red in color, (e.g., 0.415 g in 50 mL) while mixing. The mixed solution is light brown in color. The reaction flask was hand shaken for a few minutes and kept at room temperature for about one week. During this time, the flask was loosely capped. The burgundy colored crystalline particles were precipitated out on the bottom. A small portion of the crystals, with smaller particle size, were floating on the top. Filter and wash with ice water to obtain the clean crystalline burgundy particles.

C,H,N analysis results: C (11.1%), H(2.41%), N(7.97%)

melting point: 277–278° C. (decomposed)

Example 2

2:1 complex of tetrachloroplatinum (II) and N,N'-bis(2-dimethylaminoethyl)oxamide, $(CH_3)_2N(CH_2)_2N(C=O)_2N(CH_2)_2N(CH_3)_2$ A 0.01 Molar aqueous solution of N,N'-bis(2-dimethylaminoethyl)oxamide (e.g., 0.1424 g in 50 mL) was slowly added into a 0.02 M aqueous solution of potassium tetrachloroplatinum (II), light red in color, (e.g., 0.415 g in 50 mL) while mixing. The mixed solution is light brown in color. The reaction flask was hand shaken for a few minutes and kept at room temperature for about one week. During this time, the flask was loosely capped. The orange colored crystalline particles were precipitated out on the bottom and the side of the container. Filter and wash with ice water to obtain the pure crystalline orange crystals.

CHN analysis results: C(15.72%), H(3.06%), N(7.06%)

melting point: 213–214° C. (decomposed)

What is claimed is:

1. A complex of the formula (I):

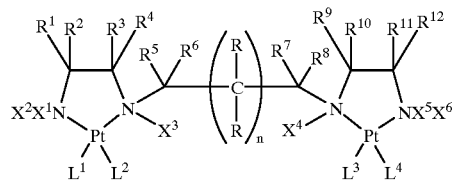

where n is 0, 1, 2, 3, 4, 5, or 6;

each of $L^1$, $L^2$, $L^3$, and $L^4$, independently, is Cl or Br;

each of R, R', $R^1$, $R^2$, $R^3$, $R^4$, $R^5$, $R^6$, $R^7$, $R^8$, $R^9$, $R^{10}$, $R^{11}$, and $R^{12}$, independently, is hydrogen, lower alkyl, lower alkoxy, alkyl carboxylate or alkyl carboxylic acid salt; or each of $CR^1R^2$ (that is, $R^1$ and $R^2$ together with the carbon which they substitute), $CR^3R^4$, $CR^5R^6$, $CR^7R^8$, $CR^9R^{10}$, $CR^{11}R^{12}$, and CRR' independently, is C=O, and each of $X^1$, $X^2$, $X^3$, $X^4$, $X^5$, and $X^6$, independently, is hydrogen, lower alkyl, alkyl carboxylate or alkyl carboxylic acid salt.

2. The complex of claim 1, which is a 2:1 complex of tetrachloroplatinum (II) and triethylenetetraamine.

3. The complex of claim 1, which is a 2:1 complex of tetrachloroplatinum (II) and N,N'-bis(2-dimethylaminoethyl)oxamide.

4. A method of treating cancer in a patient in need thereof, comprising administering a therapeutically effective amount of the complex of formula (I).

* * * * *

UNITED STATES PATENT AND TRADEMARK OFFICE
CERTIFICATE OF CORRECTION

PATENT NO. : 6,130,245
DATED : October 10, 2000
INVENTOR(S) : Jiajiu Shaw

Page 1 of 1

It is certified that error appears in the above-identified patent and that said Letters Patent is hereby corrected as shown below:

<u>Title page</u>,
Item [56], line 2, under OTHER PUBLICATIONS, after "Chemother" delete "," (comma) and substitute -- . -- (period) in its place.

<u>Claim 1</u>,
Delete entire formula and substitute with the following formula:

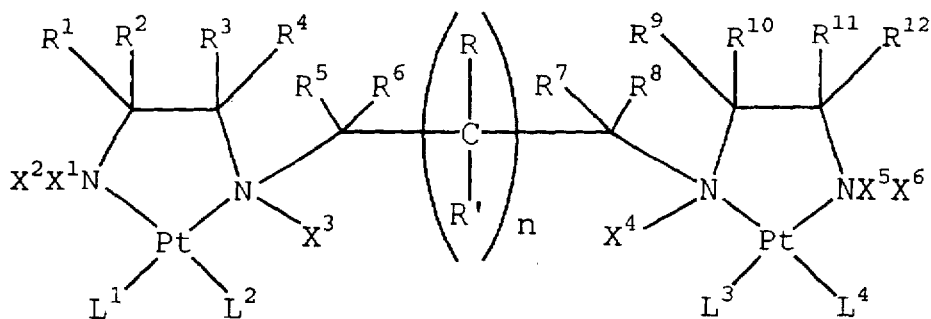

Signed and Sealed this

Ninth Day of April, 2002

Attest:

JAMES E. ROGAN
Attesting Officer    Director of the United States Patent and Trademark Office